United States Patent
Hosoi et al.

(12) 
(10) Patent No.: US 6,376,184 B1
(45) Date of Patent: *Apr. 23, 2002

(54) METHOD FOR GENE ANALYSIS

(75) Inventors: Shigeru Hosoi; Michiko Furuki, both of Shizuoka (JP)

(73) Assignee: Hamamatsu Photonics K.K., Hamamatsu (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/537,720

(22) Filed: Mar. 30, 2000

(30) Foreign Application Priority Data

Jan. 13, 2000 (JP) ........................................ 2000-022630

(51) Int. Cl.⁷ ............................ C12Q 1/68; C12P 19/34; C07H 21/02; C07H 21/04
(52) U.S. Cl. ........................ 435/6; 435/91.1; 435/91.52; 536/23.1; 536/24.32; 935/77; 935/78
(58) Field of Search .......................... 435/6, 91.1, 91.52; 536/23.1, 24.32; 935/77, 78

(56) References Cited

U.S. PATENT DOCUMENTS

| | | | |
|---|---|---|---|
| 5,503,980 A | | 4/1996 | Cantor ........................... 435/6 |
| 5,683,881 A | * | 11/1997 | Skiena ........................... 435/6 |
| 5,977,435 A | * | 11/1999 | Lefebvre et al. ............. 800/278 |
| 6,080,544 A | * | 6/2000 | Weghorst et al. ............... 435/6 |

FOREIGN PATENT DOCUMENTS

| | | | |
|---|---|---|---|
| JP | 7-203998 | 8/1995 | |
| JP | 10-243785 | 9/1998 | |
| WO | WO 99/22025 | * 5/1999 | .................... 435/6 |

OTHER PUBLICATIONS

*Stratagene Catalog*, "Gene Characterization Kits", *Stratagene Catalog*, p. 39, 1988.*

Vincent et al., "Oligonucleotides as Short as 7–Mers Can be Used for PCR Amplification", DNA and Cell Biology, vol. 13, No. 1, pp. 75–82, 1994.

The 2ⁿᵈ International Workshop on Advanced Genomics, Genomics and Drug Discovery Abstracts, Apr. 27–28, 1999 at Makuhari Meese in Chiba Pref., Japan; Hosoi et al, "DNA Sequencing by Hybridization and Extention" p. 48.

Wallace et al., 'Hybridization of Synthetic Oligodeoxyribonucleotides to $\Phi_x 174$ DNA—The Effect of Single Base Pair Mismatch', vol. 6, No. 11 (1979).

Teresa Compton, 'Degenerate Primers for DNA Amplification', PCR Protocols, A Guide to Methods and Applications, pp. 39–41, by Innis et al. (Ed.) 1990.

* cited by examiner

Primary Examiner—W. Gary Jones
Assistant Examiner—Arun K. Chakrabarti
(74) Attorney, Agent, or Firm—Leydig, Voit & Mayer, Ltd.

(57) ABSTRACT

The base sequence data of a gene is analyzed. A set of degenerate probes are hybridized to a single-stranded nucleic acid analyte derived from a gene, the nucleic acid analyte is used as a template and the probes are used as primers for a thermo-cycled polymerase reaction, the reaction products obtained from the respective probes are separated by gel electrophoresis and the electrophoresis patterns for the probes are compared, to allow for feature extraction of the base sequence of the nucleic acid analyte, including its sequencing.

9 Claims, 4 Drawing Sheets

METHOD FOR GENE ANALYSIS

BACKGROUND OF THE INVENTION

1. Field of the Invention

This invention relates generally to a method for gene analysis. More specifically, the invention relates to a method for gene analysis whereby a gene-derived single-stranded nucleic acid analyte is analyzed for a given purpose by hybridization of degenerate probes.

2. Related Background Art

In molecular biology, identification of genes, detection of gene variations and analysis of the base sequence of genes (hereunder referred to as "gene analysis") are not only important for understanding the functions and regulatory mechanisms of the genes, but also provide a practical and useful means of analysis that can be applied in the fields such as genome analysis, gene diagnosis and forensic medicine.

Gene analysis methods are largely classified into methods that are capable of detecting only the presence or absence of gene variations and methods that are capable of detecting and analyzing the actual base sequences. Examples of the methods of the former type, which have been put to use, include the method called Restriction Fragment Length Polymorphism (RFLP), which analyzes length polymorphism of nucleic acid analytes that have been fragmented by sequence specific restriction endonucleases and the method called Single Strand Conformation Polymorphism (SSCP), which, after denaturing nucleic acid analytes into single strands and then restoring the non-denaturing conditions in order to attain stable structures within the single strands, analyzes polymorphic structures by subjecting them to electrophoresis. Methods of the latter type-that have been put into use utilize partial base sequence data for a gene to synthesize the complementary strands of oligonucleotide, in which hybridization, thermo-cycled polymerase reaction, ligase reaction, etc. are carried out utilizing the discriminating power of the oligonucleotide with the specific base sequence, and the reaction product is analyzed. Also commonly employed are DNA sequencing methods such as the Sanger method and the Maxam-Gilbert method, which directly determine gene base sequences.

However, all of the methods described above suffer from drawbacks. Specifically, the former type of method gives little information on base sequence, and variation cannot necessarily be detected in all cases. The latter type of method gives base sequence data, but since such methods relay on the partial base sequence data of a given nucleic acid analyte, they are not universally applicable and cannot be used if a portion or the full length of the base sequence data is unknown.

It is, therefore, an object of this invention to provide a universal analysis method that can be applied to genes of any base sequence and that can even be applied to genes of which a portion or the full length of the base sequence data has not been obtained. It is another object to provide a method that can be applied to sequencing of nucleic acids (or genes) of lengths exceeding 1 kb, for which the Sanger method is unsuitable.

In the course of pursuing these objects, a few of the present inventors have already discovered a rapid DNA sequencing method by hybridization, and have developed a DNA sequencing apparatus employing the method (Japanese Unexamined Patent Publication HEI No. 10-243785). Because the method is a base sequence determination method, it can be used for universal gene analysis. However, in practical use the disclosed method has required oligonucleotide probes of 8 or more bases in consideration of the efficiency of polymerase reaction and the lengths that can be sequenced. This has resulted in a tremendous increase in the number of combinations of probe base sequences (i.e. the number of probes), for which reason the method is not believed to be suitable for practical use without employing fine processing technology such as DNA chips.

A possible alternative is to use electrophoresis to carry out gene analysis according to the method described above. To this end the number of base of an oligonucleotide probe (i.e. the probe base length) must be no greater than 7, and preferably as small as about 3, 4 or 5. The number of possible probe combinations is 64 in the case of 3 bases, 256 in the case of 4 bases and 1024 in the case of 5 bases. If oligonucleotide probes of such short length are used, the method can be satisfactorily accomplished even using currently available electrophoresis apparatuses. However, since a hybridizable site appears on an average of once every 64 bases for a 3-base length, once every 256 bases for a 4-base lenght and once every 1024 bases for a 5-base length, multiple probe-complementary sites will be present when it is attempted to sequence nucleic acid analytes that are over 1 kb long using the aforementioned oligonucleotide probes, and this presents a problem that renders it unsuitable for methods employing DNA chips. Also, when such short oligonucleotide probes are used for polymerase reaction, the melting point of the double-stranded nucleic acid produced with the oligonucleotide probe as such and the annealing temperature onto the nucleic acid analyte are extremely low. The melting point $T_m$ is calculated by one of the following equations according to three known methods.

Nearest neighbor method (1)

%GC method ($T_m$=81.5° C.+16.6(log $M$)+0.41(%$GC$)−0.61(%form)−500/$L$) (2)

2+4 method ($T_m$=2($A$+$T$)+4($G$+$C$)) (3)

When estimated according to the 2+4 method that is often used for short oligomers, for a 3-base length: $T_m$=6–12° C., for a 4-base length: $T_m$=8–16° C., and for a 5-base length: $T_m$=10–20° C.

Since the temperature for achieving hybridization is usually to be set at 10° C. or even lower than the annealing temperature, the hybridization must be conducted almost freezing temperature, and the DNA polymerase, including Taq polymerase (optimal temperature: 72° C.) that is used for the thermo-cycled polymerase reaction amplification is virtually inactive at such a low temperature. Consequently, when oligonucleotide probes are used with such base lengths, they are indeed unlikely to achieve gene analysis.

SUMMARY OF THE INVENTION

In order to overcome the problems described above, this invention provides a method for gene analysis by hybridization that is universally applicable.

Specifically, according to a first aspect of this invention there is provided a method for gene analysis by hybridization comprising:

a first step of preparing a set of degenerate probes;

a second step of hybridizing a single-stranded nucleic acid analyte derived from the gene to each probe of the set of degenerate probes;

a third step of using the hybridized nucleic acid analyte as a template and each of the probes as a primer to carry out a thermo-cycled polymerase reaction;

a fourth step of separating the reaction product obtained from each probe by gel electrophoresis to obtain an electrophoresis pattern; and a fifth step of comparing the electrophoresis patterns for each of the probes.

According to another aspect of the invention there is provided a method for gene analysis by hybridization comprising:

a first step of preparing a set of degenerate probes; each probe having a prescribed base sequence, a second step of hybridizing a single-stranded nucleic acid analyte derived from the gene to each probe of the set of degenerate probes;

a third step of using the hybridized nucleic acid analyte as a template and each of the probes as a primer to carry out a thermo-cycled polymerase reaction, and extending the primer;

a fourth step of separating the extension reaction product obtained from each of the probes into extension fragments by gel electrophoresis, and determining the base length of each of the extension fragments; and a fifth step of correlating the base lengths of the extension fragments with the prescribed base sequence of each of the probes to characterize the base sequence of the nucleic acid analyte.

According to yet another aspect of the invention there is provided a method for gene analysis by hybridization comprising:

a first step of preparing a set of degenerate probes, each probe having a prescribed base sequence;

a second step of hybridizing a single-stranded nucleic acid analyte derived from the gene to each probe of the set of degenerate probes;

a third step of using the hybridized nucleic acid analyte as a template and each of the probes as a primer to carry out a thermo-cycled polymerase reaction, and extending the primer;

a fourth step of separating the extension reaction product obtained from each of the probes into extension fragments by gel electrophoresis, and determining the base length of each of the extension fragments; and a fifth step of aligning the prescribed base sequence of each of the probes in the order of the base length of the extension fragment according to a Eulerian path-finding algorithm, to determine a portion of the base sequence of the nucleic acid analyte.

Preferably, the full length base sequence of the nucleic acid analyte is determined in the method for gene analysis described above.

The invention further provides the method for gene analysis as described above wherein each of the probes is an oligonucleotide represented by $N_1N_2N_3 \ldots N_nX_1X_2 \ldots X_m$ (formula 1), $N_1N_2N_3 \ldots X_1X_2 \ldots X_mN_n$ (formula 2), $N_1N_2N_3 \ldots X_1X_2 \ldots X_mN_{n-1}N_n$ (formula 3), . . . or $X_1X_2 \ldots X_mN_1N_2N_3 \ldots N_{n-1}N_n$ (formula n) (where $N_1$–$N_n$ designate any of the four bases A, T, G and C but are random, $X_1$–$X_m$ designate any of A, T, G and C but are predetermined, and m and n are each a natural number).

The invention still further provides any of the above methods for gene analysis wherein the set of degenerate probes is the set of all of the $4^m$ combinations comprising each of the aforementioned probes, or a partial subset thereof.

Here, m is preferably 3, 4 or 5.

More preferably, n is 5, 6, 7 or 8.

Most preferably, m is 4 and n is 6.

The invention still further provides any of the above methods for gene analysis wherein in the first step there is prepared an array vessel having a number of wells corresponding to the total number of the set of degenerate probes, and each probe of the set of degenerate probes is fractionally dispensed into one of the wells.

The invention still further provides the method for gene analysis as described above wherein each of the probes is as defined above, and the total number of the set of degenerate probes is $4^m$.

The invention still further provides a gene analysis kit comprising:

a set of degenerate probes each probe of which is an oligonucleotide represented by $N_1N_2N_3 \ldots N_nX_1X_2 \ldots X_m$ (formula 1), $N_1N_2N_3 \ldots X_1X_2 \ldots X_mN_n$ (formula 2), $N_1N_2N_3 \ldots X_1X_2 \ldots X_mN_{n-1}N_n$ (formula 3), . . . or $X_1X_2 \ldots X_mN_1N_2N_3 \ldots N_{n-1}N_n$ (formula n) (where $N_1$–$N_n$ designate any of the four bases A, T, G and C but are random, $X_1$–$X_m$ designate any of A, T, G and C but are predetermined, and m and n are each a natural number);

an array vessel having a number of wells corresponding to the total number of the set of degenerate probes;

a buffer solution; and

DNA polymerase, wherein each of the probes is fractionally dispensed in one of the wells of the array vessel.

The invention still further provides the gene analysis kit as described above wherein each of the dispensed probes is immobilized on one well of the array vessel.

According to the method for gene analysis of this invention, degenerate probes are used for hybridization with a single-stranded nucleic acid analyte derived from a gene, the nucleic acid analyte is used as a template and the probes are used as primers to carry out a thermo-cycled polymerase reaction, the reaction products obtained from the respective probes are separated by gel electrophoresis and the electrophoresis patterns are compared; therefore, it allows the feature of base sequence of the gene to be extracted without sequencing the entire base sequence thereof.

Also, according to the gene sequencing method of the invention, degenerate probes are used for hybridization with a single-stranded nucleic acid analyte derived from a gene, the nucleic acid analyte is used as a template and the probes are used as primers to carry out a thermo-cycled polymerase reaction and to extend the primers, the extension reaction products obtained from the respective probes are separated into extension fragments by gel electrophoresis, the base length of each extension fragment is determined and the base lengths of the extension fragments are correlated with the prescribed base sequence of each probe to characterize the base sequence of the nucleic acid analyte; therefore it allows the feature of base sequence of the gene to be extracted with the need of sequencing only a part thereof and without sequencing the entire base sequence thereof.

Furthermore, according to the gene sequencing method of the invention, degenerate probes are used for hybridization with a single-stranded nucleic acid analyte derived from a gene, the nucleic acid analyte is used as a template and the probes are used as primers to carry out a thermo-cycled polymerase reaction to extend the primers, the extension reaction products obtained from the respective probes are separated into extension fragments by gel electrophoresis, the base length of each extension fragment is determined and the prescribed base sequence of each probe is aligned in the order of the base length of the extension fragment according to the Eulerian path-finding algorithm to determine a portion of the base sequence of the nucleic acid analyte; therefore, it allows the base sequence to be determined visually in a relatively simple manner. Moreover, the present method allows the full length base sequence of the nucleic acid analyte to be determined without cloning.

The method for gene analysis of the invention is therefore widely and universally applicable to not only sequencing but also gene identification, gene variation detection and other purposes of gene base sequence data analysis. More specifically, it can be applied to gene diagnosis (infection, cancer, genetic diseases and the like) and gene-related drug development (drug discovery, gene screening), as well as in general gene detection- related fields (drugs, foods, agriculture, environment, etc.).

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

BRIEF DESCRIPTION OF THE DRAWINGS

FIG. 1 contains charts showing electrophoresis patterns for thermo-cycled polymerase reaction products obtained as a result of repeated polymerase reactions with a nucleic acid analyte using different degenerate probes according to the invention.

FIG. 1E corresponds to probe $N_1N_2N_3N_4N_5N_6GCAA$,

FIG. 1F to probe $N_1N_2N_3N_4N_5N_6GCAT$,

FIG. 1G to probe $N_1N_2N_3N_4N_5N_6GCAG$ and

FIG. 1H to probe $N_1N_2N_3N_4N_5N_6GCAC$. The peaks in each of the charts represent the separated fragments. The horizontal scale in the charts represents fragment base length, and the vertical scale represents fragment intensity (arbitrary units).

FIG. 2 contains charts showing electrophoresis patterns for thermo-cycled polymerase reaction products obtained as a result of polymerase reactions with a nucleic acid analyte using different degenerate probes according to the invention.

FIG. 3 is a graphical illustration of a technique of sequencing the region near base No. 650 of the nucleic acid analyte, according to the sequencing method of this invention. Sequencing is accomplished by reading the bases successively from left to right. The numerals in the illustration represent the actual measured base lengths of the extension fragments obtained from the extension reaction products using the respective probes.

FIG. 4 is a graphical illustration of a technique of sequencing the region near base No. 1050 of the nucleic acid analyte, according to the sequencing method of the invention. Sequencing is accomplished by reading the bases successively from left to right. The numerals in the illustration represent the actual measured base lengths of the extension fragments obtained from the extension reaction products using the respective probes.

DESCRIPTION OF THE PREFERRED EMBODIMENTS

Figure 1E:
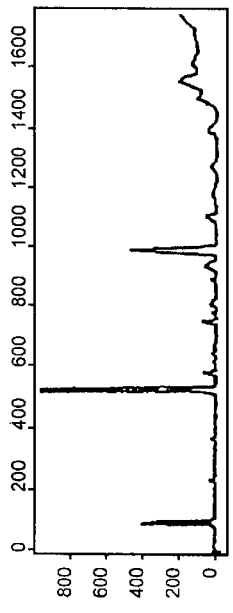
FIGS. 1E to 1H are charts showing the results for repeated thermo-cycled polymerase reactions.
Figure 1F:
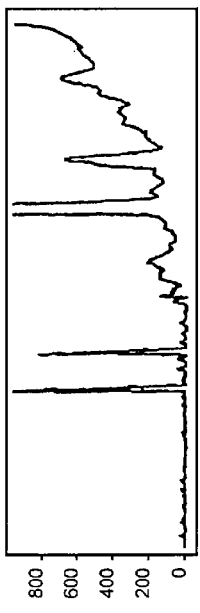
Figure 1G:
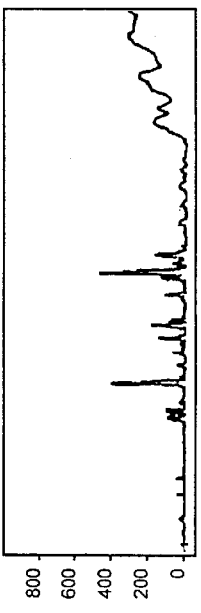
Figure 1H:
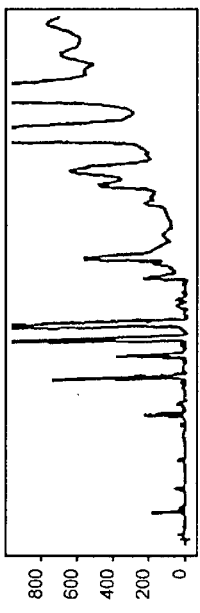
Figure 1A:
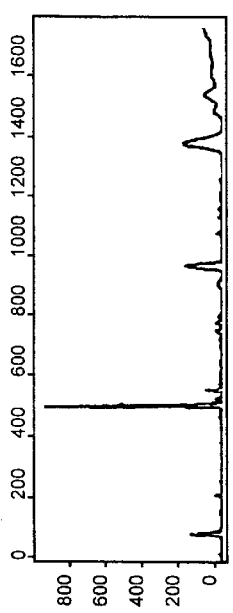
FIG. 1A corresponds to probe $N_1N_2N_3N_4N_5N_6GCAA$.
Figure 1B:
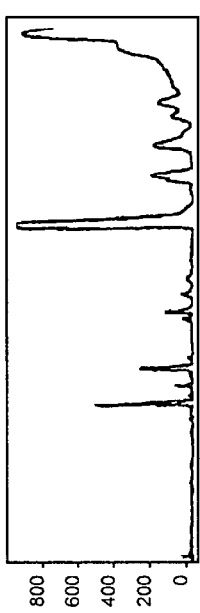
FIG. 1B to probe $N_1N_2N_3N_4N_5N_6GCAT$.
Figure 1C:
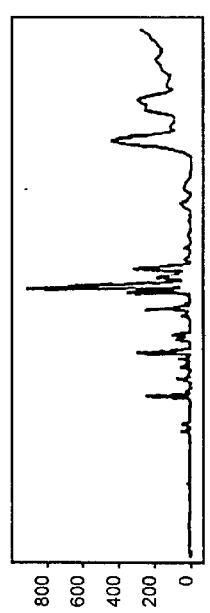
FIG. 1C to probe $N_1N_2N_3N_4N_5N_6GCAG$.
Figure 1D:
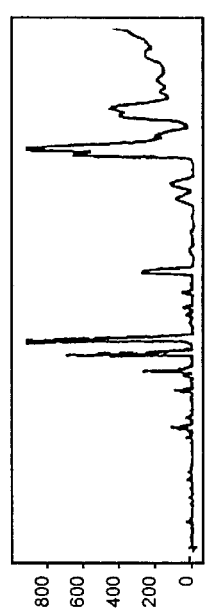
FIG. 1D to probe $N_1N_2N_3N_4N_5N_6GCAC$.

This invention will now be explained in further detail.

The principal aspect of the invention is a method for gene analysis by hybridization comprising:

a first step of preparing a set of degenerate probes;

a second step of hybridizing a single-stranded nucleic acid analyte derived from the gene to each probe of the set of degenerate probes;

a third step of using the hybridized nucleic acid analyte as a template to carry out a thermo-cycled polymerase reaction;

a fourth step of separating the reaction product obtained from each probe by gel electrophoresis to obtain an electrophoresis pattern; and a fifth step of comparing the electrophoresis patterns for each of the probes.

Throughout the present specification, the term "gene-derived single-stranded nucleic acid analyte" refers to coding strand or non-coding strand DNA that is one of the strands of double-stranded cDNA composing a gene, or to mRNA transcribed from coding strand DNA, and it will encompass analytes isolated from tissues or cells and analytes synthesized by gene manipulation technology or artificially.

Also, throughout the present specification the term "set of degenerate probes" refers to a set of probes each having a constant portion with a prescribed base length (i.e., a specific base sequence portion) and a variable portion with a prescribed base length (i.e., a portion wherein the base sequence comprises a random combination of the 4 bases). In addition, the term "having a prescribed base sequence" used throughout the specification means that the constant portion of the probe has a predetermined base sequence. Each individual probe is any oligonucleotide probe represented by $N_1N_2N_3 \ldots N_nX_1X_2 \ldots X_m$ (formula 1), $N_1N_2N_3 \ldots X_1X_2 \ldots X_mN_n$ (formula 2), $N_1N_2N_3 \ldots X_1X_2 \ldots X_mN_{n-1}N_n$ (formula 3), ... or $X_1X_2 \ldots X_mN_1N_2N_3 \ldots N_{n-1}N_n$ (formula n) (where $N_1$–$N_n$ designate any of the four bases A, T, G and C but are random, $X_1$–$X_m$ designate any of A, T, G and C but are predetermined, and m and n are each a natural number). A mixture of such probes will be considered a set of degenerate probes for use in the method for gene analysis of the invention, and the probes may be easily synthesized by a method well-known to those skilled in the art using, for example, a commercially available automatic DNA synthesizer (Model No. 381 by PE Applied Biosystems Inc.). The first step of the method for gene analysis of the invention is accomplished in this manner.

The constant portion of the probe represented by $X_1X_2 \ldots X_m$ has a prescribed base sequence and discriminates nucleic acid analyte base sequences that are complementary thereto by hybridization. Thus, the discriminating power extends for m bases, although the probe itself has a length of m+n bases. Preferably, m is an integer of 3 to 7 and n is an integer of 5 to 8. For example, when m is 3, 4 or 5 and n is limited to 7, 6 or 5 respectively, the length of the probe itself will be 10 bases, and estimation of the $T_m$ by the aforementioned 2+4 method gives $T_m$=20–40° C. Consequently, the $T_m$ falls in a range that is sufficiently practical for a thermo-cycled polymerase reaction. Moreover, the probe synthesis will only require about 64, 256 or 1024 different types, respectively.

When degenerate oligonucleotide probes are actually used, however, only a small portion of the probe mixture has a base sequence completely matching the nucleic acid analyte at the variable portion of $N_1N_2N_3 \ldots N_n$. For example, when n=6, the probability of a probe with the desired base sequence is 1 out of 4096. This raises a number of problems involving, specifically, (1) whether or not an adequate amount of completely matching probes can be guaranteed for the thermo-cycled polymerase reaction, (2) whether or not mismatching of probes other than completely matching probes will affect the analysis results, and (3) possible reduced reaction efficiency in the thermo-cycled polymerase reaction with the nucleic acid analyte due to primer-dimer formation between probes. It has also been pointed out that short base length probes may not be suitable for sequencing (base sequence determination) because of the reduced discriminating power for complementary sequences when short bases sequences are used. Based on experimental results that will be presented in the Examples, a degenerate probe according to the invention is designed such that m is in the range of 3–5 and n in the range of 5–8. Thus, the total number of probes used will preferably be 64 for 3 bases, 256 for 4 bases and 1024 for 5 bases, and depending on the purpose (for example, for detection of 3-base repeats), only a portion thereof may sometimes be used as a subset. In any case, by allowing the degenerate probes to hybridize to complementary partial sequences contained in the nucleic acid analyte and using them as primers for a thermo-cycled polymerase reaction, a universally applicable gene analysis method can be realized. Because of the problems mentioned above, prior to this invention such approach had not been recognized by those skilled in the art as being applicable to gene analysis.

In the second step of the method for gene analysis so of the invention, the single-stranded nucleic acid analyte is hybridized to the set of degenerate probes. Specifically, the nucleic acid analyte is mixed with the probes and the conditions are set so as to maximize hybridization of only the completely matching probes. Then, a manipulation such as washing is used to remove the non-hybridized probes. The hybridization conditions employed here are selected in consideration of the probe base length, the GC content of the probes, etc., and those skilled in the art can easily select the appropriate conditions for specific embodiments, based on the published literature. In the method for gene analysis of the invention, mere mismatching of hybridization is not a critical problem, but it is preferably kept to a minimum from the standpoint of analysis precision and reproducibility.

In the third step of the method for gene analysis of the invention, the nucleic acid analyte that has hybridized to the probe is used as a template for a thermo-cycled polymerase reaction (extension reaction) and the probe is used as a primer. Here, there are no particular limitations on the type of polymerase used for the reaction or the reaction conditions, and those skilled in the art can easily select the appropriate conditions for specific embodiments, based on the published literature.

The second and third steps are carried out in a reaction vessel suited for the thermo-cycled polymerase reaction, but there are no particular limitations on the shape or material of the vessel. However, since a very large number of probe types are used, it is necessary for the vessel to be capable of housing them separately. According to a preferred embodiment of the invention, an array vessel is prepared having a number of wells corresponding to the total number of the set of degenerate probes (preferably $4^m$), and each probe of the set of degenerate probes is fractionally dispensed into one of the wells. More preferably, each of the probes is immobilized on the one well. A specific example of such a reaction vessel is one constructed by preparing Eppendorf-type tubes of appropriate size in a number corresponding to the number of wells required, and combining them. Alternatively, a commercially available 96-well microplate may be used as such, or multiplate microplates may even be combined for use as the vessel. According to the sequencing method disclosed in Japanese Unexamined Patent Publication HEI No. 7-203998, it is necessary to prepare $4^{m+n}$ wells, assuming the probe in formula (1) is not a degenerate probe. However, this number turns out to be $4^m$ for the method for gene analysis of this invention, and this is more practical.

Another embodiment of this invention is a gene analysis kit comprising the above-mentioned array vessel with the addition of a set of degenerate probes, a buffer solution, DNA polymerase, etc., wherein each of the probes is fractionally dispensed into one well of the array vessel. As explained above, each of the probes is preferably immobilized on the one well of the array vessel.

In the fourth step of the method for gene analysis of the invention, the thermo-cycled polymerase reaction products obtained in the third step are separated by gel electrophoresis (high resolution agarose gel, etc.) to obtain electrophoresis patterns. The electrophoresis apparatus used therefor may be a standard apparatus used for sequencing by the Sanger method. Since a certain degree of reading error is permissible when it is not necessary to sequence a further separated thermo-cycled polymerase reaction product by the method for gene analysis of the invention, it is preferred in practice for the electrophoresis to be done only a short time so that the migration pattern can be taken as a single image. The electrophoresis conditions (agarose concentration, voltage, migration time, etc.) may be easily selected by those skilled in the art according to common protocol.

In the subsequent fifth step of the method for gene analysis of this invention, the electrophoresis patterns obtained in the fourth step for each probe (a pattern being obtained for each of the probe combinations) are compared. The comparison (i.e. analysis) of the electrophoresis patterns can sometimes be made visually, but depending on the purpose of the analysis it is preferred to use an algorithm and software suited for the method for gene analysis of the invention. The analysis software may be pattern recognition software or neural network software, for gene identification. If the purpose is detection of gene variation, the electrophoresis pattern of the normal gene may be used as the basis from which subtraction analysis is performed on the gene of interest including the nucleic acid analyte. By extracting the difference it is possible to detect variation or other anomalies. Thus, software analysis of the electrophoresis patterns and automization thereof are also one embodiment of the method for gene analysis of the invention.

The fifth step will have different modes depending on the type of gene analysis attempted. According to a particularly preferred embodiment, analysis of the electrophoresis patterns allows feature extraction of the base sequence of a gene. For example, by the Sanger method, the base sequence of a nucleic acid analyte of a few kilobases in length can only be determined by subcloning. Furthermore, most of the prior art gene analysis methods cannot be used in cases where sequence data has not been obtained in advance. The analysis method of this invention can be applied even under such circumstances. Moreover, the range of applications is wider, including gene identification, species identification, cDNA identification, analysis of gene variation, SNP and gene polymorphism, and diagnosis of genetic diseases such as 3-base repeat disease.

According to another aspect of the invention, there is provided more concrete means for accomplishing the gene analysis described above. That is, it includes a step of separating the extension reaction products obtained by the third step into extension fragments by gel electrophoresis, and determining the base lengths of the extension fragments. This is usually accomplished by appropriately setting the electrophoresis conditions on the electrophoresis apparatus. Well-resolved peaks corresponding to numerous extension fragments will then appear at the respective base length positions (see FIGS. 1, 2). The extension fragment base lengths are then correlated with the prescribed base sequence of the probe. As explained above, the prescribed base sequence of the probe recognizes the sequence of the nucleic acid analyte, and therefore obtaining a specific extension fragment indicates the presence in the nucleic acid analyte of a sequence complementary to that specific base sequence. In addition, the extension fragment base length should match the degree of extension in the 5' to 3' direction of the primer (or probe). Thus, if the base length of an extension fragment correlates with the prescribed base sequence of the probe, then a sequence complementary to the prescribed base sequence is present at the location distanced from the 5' end of the base sequence of the nucleic acid analyte by a portion equal to the base length of the fragment. If this procedure is repeated for a number of probes, it will be possible to characterize the base sequence of the nucleic acid analyte itself. This specific embodiment is useful for identification of 3-base repeats (repeating sequences, such as CAG or CTG). Such sequences are known to be amplified through succeeding generations, causing onset of genetic diseases such as Huntington's chorea and myotonic dystrophy. It is also a powerful means for identification of gene tags (also known as expressed sequence tags). If desired, this embodiment can also be applied in combination with the Sanger method or other sequencing methods to determine portions or the entirety of base sequences of extension fragments of interest.

According to yet another aspect of the invention there is provided a more concrete means for accomplishing the gene analysis described above. That is, it also includes a step of separating the extension reaction products obtained by the third step into extension fragments by gel electrophoresis, and determining the base length of each of the extension fragments. The specific base sequence of each probe is then aligned in the order of extension fragment base length according to the Eulerian path-finding algorithm, and a portion of the base sequence of the nucleic acid analyte is determined. In principle, this approach is exactly the same as the sequencing method disclosed in Japanese Unexamined Patent Publication HEI No. 7-203998. According to this publication, specifically, the degree of extension in the 5' to 3' direction of the primers (or probes) is measured either biochemically or enzymatically, the primers are aligned based on the degree of extension, and the base sequence of the nucleic acid analyte is determined from the base sequences of the primers. Since according to the invention the probe sequences are aligned based on the base lengths of the extension fragments, it is possible to accomplish sequencing more accurately than the method of the aforementioned publication despite reading error of fragment base lengths due to the electrophoresis apparatus. Thus, as will be illustrated by the Examples, it is possible to determine portions or the full length of the base sequence of a nucleic acid analyte (1 kb or longer) without resorting to cloning.

This invention will now be explained in further detail by way of examples; however, these examples are not intended to limit the invention.

EXAMPLES

Production Example: Preparation of Single-stranded Nucleic Acid Analyte

A portion (approximately from 7 to 9 kb) of λDNA (approximately 48 kb) was amplified by the asymmetric polymerase chain reaction method for use as a nucleic acid analyte. The primers used were λ1 (set forth in SEQ ID NO: 1) and λ2 (set forth in SEQ ID NO: 2). The polymerase chain reaction conditions comprised 30 cycles, one cycle being reaction for one minute at 94° C. followed by 20 seconds at 98° C. and then by one minute at 68° C. This was followed by an additional 10 minutes of extension reaction at 72° C.

| | |
|---|---|
| λDNA | 50 pg |
| λ1 (10 pmole/μl) | 2 μl |
| λ2 (0.1 pmole/μl) | 2 μl |
| Ready-To-Go ® Polymerase Chain Reaction Mix | 1 tablet |
| Distilled water | |
| Total: | 25 μl |

The main components used for dissolution of the polymerase chain reaction mix in 25 μl of distilled water were the following: 1.5 U Taq, 10 mM Tris-HCl (pH 9.0, room temperature), 50 mM KCl, 1.5 mM $MgCl_2$, 200 μM dNTP.

After amplification by the polymerase chain reaction, the excess primers and nucleotides were removed using ethanol precipitation and a spin column (G-50 Microcolumn), and the polymerase chain reaction product was purified. The resulting single-stranded nucleic acid had a base length of 2002, and its base sequence is set forth in SEQ ID NO: 3. This nucleic acid was dissolved in distilled water as a nucleic acid analyte, and prepared to a concentration of about 100 ng/μl based on the OD value ($A_{260}$) at 260 nm for use in the following experiment.

Example 1

Thermo-cycled Polymerase Reaction and Electrophoresis of Extension Reaction Product 1.1 Experimental Procedure A thermo-cycled polymerase reaction was conducted using a mixture of the nucleic acid analyte, the degenerate probes specified below, polymerase enzyme, nucleotides, buffer solution and fluorescently-labeled dUTP, with the temperature cycle and solution composition set forth below.

| Cycle extension reaction mix (per sample) | |
|---|---|
| Nucleic acid analyte | 10 μl |
| Degenerate probe (100 pmol/2 μl) | 5 μl |
| Ready-To-Go ® Polymerase Chain Reaction Mix | 1 tablet |
| Thermo Sequenase | 3.2 U |
| R6G-dUTP (100/μM) | 0.5 μl |
| Distilled water | |
| Total: | 25 μl |

The temperature cycle was a cycle of one minute of annealing at 96° C. followed by 30 seconds at 96° C., 15 seconds at 20° C. and 4 minutes at 60° C., repeated 20 times. The thermo-cycled polymerase reaction product from each probe was further purified with a microcolumn (G-50) and subjected to electrophoresis under denaturing conditions, and the fragments were analyzed. The electrophoresis was carried out according to the standard protocol for the ABI Genetic Analyzer 310. GeneScan™ ver2.1 was used for the fragment size analysis. Examples of the electrophoresis patterns obtained are shown in FIGS. 1 and 2.

1.2 Reproducibility of Extension Reaction

In order to determine the reproducibility of the extension reaction when the thermo-cycled polymerase reaction was conducted according to the protocol described in 1.1 above, the experiment was repeated twice using the four kinds of degenerate probe, $N_3N_2N_3N_4N_5N_6$GCAA (SEQ ID NO: 4), $N_1N_2N_3N_4N_5N_6$GCAT (SEQ ID NO: 5), $N_1N_2N_3N_4N_5N_6$GCAG (SEQ ID NO: 6) and $N_1N_2N_3N_4N_5N_6$GCAC (SEQ ID NO: 7). Analysis of the experimental results revealed that extension reaction did not occur for all of the complementary sequences of the nucleic acid analyte, but that the reaction actually occurred at only from about ⅓ to about half of the reaction sites among the complementary sequences. However, those locations are essentially fixed, and it was found that hybridization of the same set of probes to the same nucleic acid analyte under the same experimental conditions gave an almost invariable characteristic electrophoresis pattern (see FIG. 1, comparing, for example, FIGS. 1A and 1B).

1.3 Relationship Between Number (n) of Ns (Variable Portion $N_1 \ldots N_n$ of Degenerate Probe) and Their Locations in the Probe Sequences For hybridization, it is recognized that the probe length that can completely prevent mismatching under optimized experimental conditions such as annealing temperature is a base length of at least 12. In the case of the degenerate probes of the invention, if the constant portion with discriminating power is 4 bases long, for example, the length of the variable portion should be at least 8 bases long in order to minimize mismatching. As considered above, however, when such an oligonucleotide probe is actually used, increasing the number of Ns results in a situation in which only a very limited number of the variable portion sequences in the probe mixture completely match sites of the nucleic acid analyte. Consequently, the optimum probe length for use in gene analysis should be experimentally determined. When the Ns are serially connected it can be expected that primer-dimer complexes with higher temperature stability tend to be formed. One way of effectively preventing this is to bring the constant portion $X_1 \ldots X_m$ in the midst of the variable portion $N_1 \ldots N_n$, thus reducing as much as possible the number of connected Ns.

Therefore, three kinds of degenerate probes with a different number of Ns, $N_1N_2N_3N_4N_5N_6N_7N_8$ATGC (SEQ ID NO: 8), $N_1N_2N_3N_4N_5N_6$ATGC (SEQ ID NO: 9) and $N_1N_2N_3N_4$ATGC (SEQ ID NO: 10), were prepared and used in a thermo-cycled polymerase reaction according to the protocol described in 1.1. Judging from the number of extension fragments theoretically predicted among this set (base lengths of 353, 393, 1254, 1404, 1478, and 1616) and the heights of the peaks, $N_1N_2N_3N_4N_5N_6$ATGC was found to be most advantageous from the standpoint of fewer excess extension fragments and more theoretically predicted extension fragments (FIG. 2A).

In addition, two kinds of degenerate probes, $N_1N_2N_3N_4$ATGC$N_5N_6N_7N_8$ (SEQ ID NO: 11) and $N_1N_2N_3$ATGC$N_4N_5N_6$ (SEQ ID NO: 12), having different variable portion arrangements were also prepared and used in a thermo-cycled polymerase reaction according to the protocol described in 1.1. Upon comparing these with $N_1N_2N_3N_4N_5N_6$ATGC, virtually the same results for the number of theoretically predicted extension fragments and peak heights were obtained for $N_1N_2N_3N_4N_5N_6$ATGC and $N_1N_2N_3$ATGC$N_4N_5N_6$, despite the fact that $N_1N_2N_3$ATGC$N_4N_5N_6$ had the greatest number of extension fragments.

A larger number of extension fragments generally tends to give more extension fragments other than the theoretical ones, but all of the four kinds of probes other than $N_1N_2N_3N_4$ATGC were shown to exhibit a characteristic electrophoresis pattern. These are therefore suitable for use in gene analysis.

It was also found that changing to a completely different nucleic acid analyte gave a different electrophoresis pattern when the above-mentioned experiment was repeated. These results demonstrated that comparison of electrophoresis patterns for the respective probes allows inference of the features and types of genes with different base sequences.

Example 2

Sequencing of Nucleic Acid Analyte

A portion (2002 bases long) of the single-stranded λDNA prepared in the production example was used as a nucleic acid analyte, a combination of 256 different 4-base degenerate probes similar to those used in Example 1 (a constant portion of 4 bases and a variable portion of 6 bases: $N_1N_2N_3N_4N_5N_6$ATGC, etc.) were used in an attempt to determine the base sequence by the sequencing method of the invention. Before sequencing, it was first necessary to confirm the precision or reliability of the sequencing. SBH methods, including the present method, have a drawback of mismatching during hybridization, and even probes that are not fully complementary will hybridize with the nucleic acid analyte. This can pose a serious problem for sequencing.

2.1 Verification of Mismatching

In the same manner as the method in Example 1 (1.1), hybridization of the nucleic acid analyte and the degenerate probes was followed by thermo-cycled polymerase reaction, and the resulting thermo-cycled polymerase reaction products were subjected to electrophoresis and the fragments were analyzed. Analysis of all of the separated fragments gave the following results: complete match (50.4%), 1-base mismatch (36.2%), 2-base mismatch (12.0%), unknown (1.3%). Consequently, since most of the extension fragments were complete matches or 1-base mismatches and on this basis an extension reaction occurred, this indicated that the fragments could be used for sequencing adequately.

Next, the frequency of mismatching was examined for a 1000-base long extension reaction site from base length 100 to base length 1100 of the nucleic acid analyte. The results revealed 736 completely matching sites, 528 1-base mismatching sites and 196 2-base or more mismatching sites (with some overlapping sites; for example, one site had only one mismatch while another site had one complete match and one 1-base mismatch, etc.) The sites at which extension reaction occurred with complete matches and 1-base mismatches comprised about 96% of the total length. The sites at which extension reaction did not readily occur were sites such as, for example, TTTTTT and AAAAAA. Thus, it was demonstrated that for the specific base length portion mentioned above, an even higher proportion of complete matches or 1-base mismatches can be expected, giving a considerable degree of sequencing precision.

2.2 Sequencing

As the mismatch verification in 2.1 showed that sequencing of a nucleic acid analyte is actually possible by this method, sequencing was then undertaken for the portion from base length 100 to base length 1100 of the above-mentioned nucleic acid analyte. This was based on the "Eulerian path-finding algorithm" method disclosed in Japanese Unexamined Patent Publication HEI No. 7-203998. Specifically, sequencing can be accomplished by measuring the lengths of the extension fragments containing the probe sequences (the base lengths according to electrophoresis), and aligning in order of length (from short to long) of the extension fragments.

In current electrophoresis methods, however, fragment sizes have an error of from a few to about 10 bases, and reliable visual sequencing can only be achieved when there is connected 3 base-overlaps. In the experimental results for the present example, about 70% consisted of overlapping portions of 3 bases each between each of the 4 base sequences (corresponding to the 4-base constant portions of the degenerate probes). The base sequence can be read for sequencing even with 1-base mismatches included in these overlapping portions. However, if the fragment size measurement is more accurate even without overlapping, sequencing is still possible since the sequence will be connected at portions other than the 3-base overlaps.

Figure 3:
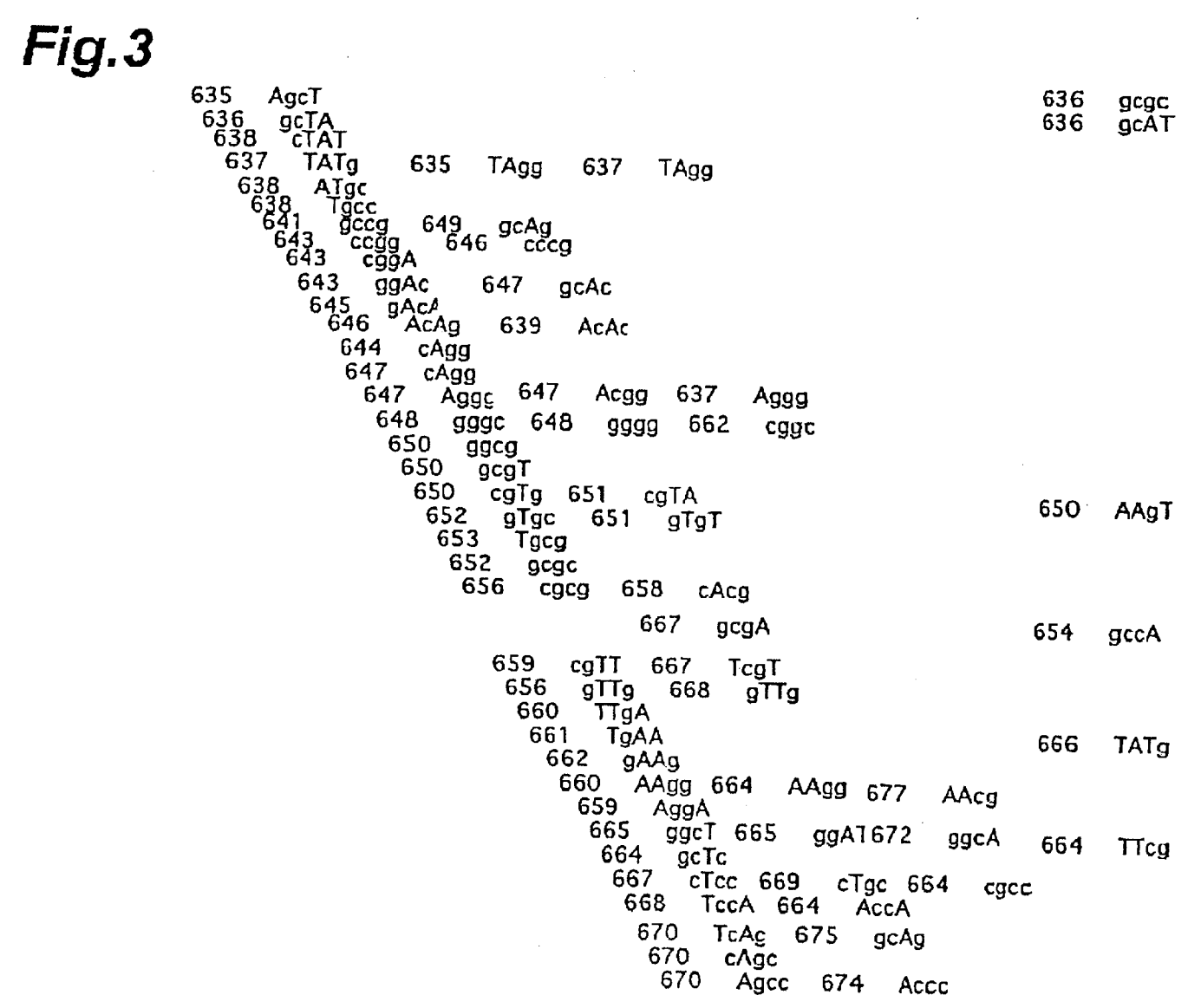
Figure 4:
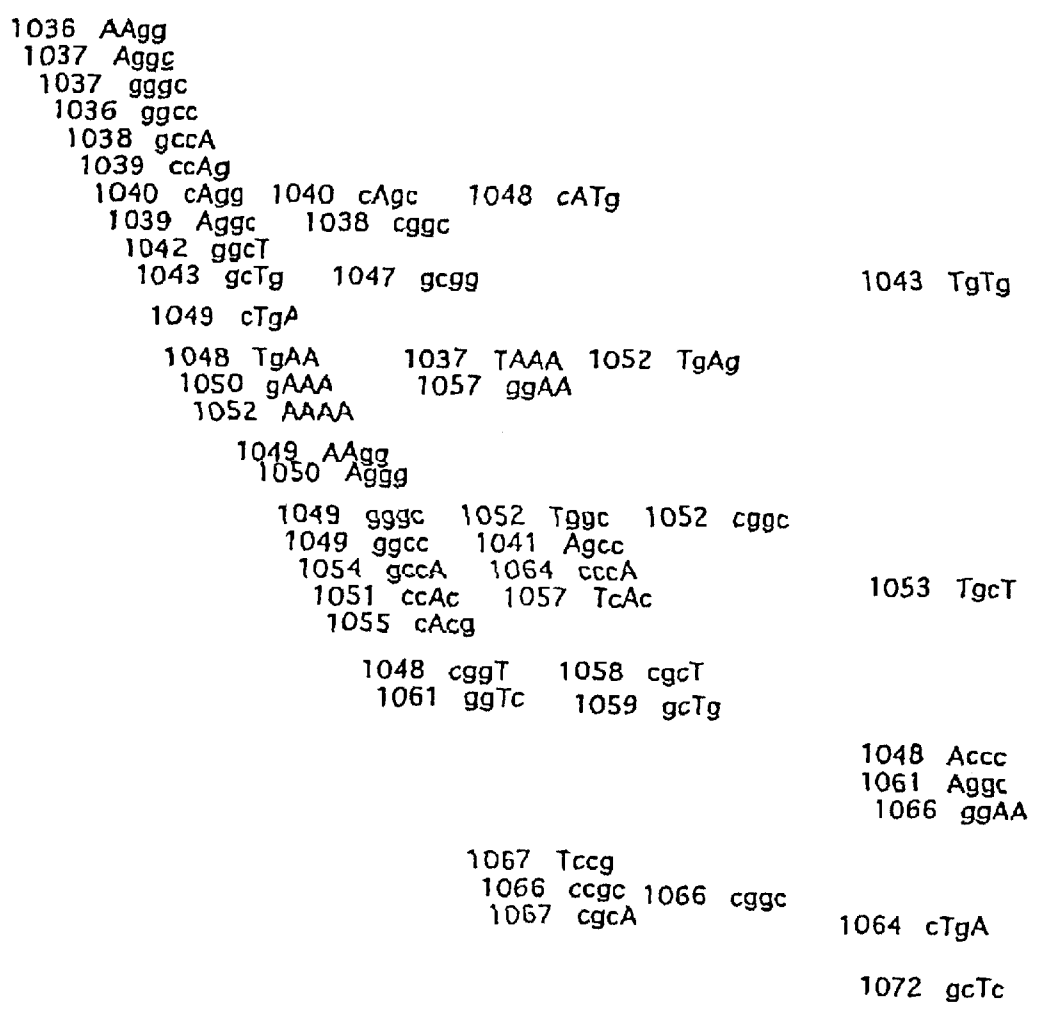

When the extension fragments corresponding to base lengths near base 650 and near base 1050 of the nucleic acid analyte are actually aligned in order of base length shortness, according to the Eulerian path-finding algorithm, the layouts shown in FIG. 3 and FIG. 4 are obtained. Here, the portions without 3-base overlapping are shown to the right outside of the base-aligned groups. The 3-base overlap portions are successively matched up and the overlapping portions are read in order (from the 5'-end to the 3'-end, i.e. from left to right), so that the sequences described below can be predicted.

vicinity of base 650
AGCTATGCCGGACAGGGCGTGCGCG
CGTTGAAGGCTCCAGCC
vicinity of base 1050
AAGGGCCAGGCTGAAAA
AAGGGCCACG
CGGTC Since both of these sequences are actually included in the nucleic acid analyte (see SEQ ID NO: 3 in the Sequence Listing), sequencing was shown to be possible by the present method. The above base sequences are set forth as SEQ ID Nos: 13 to 16 in the Sequence Listing. Similar visual 3-base overlap sequencing was carried out from base 100 to base 1100, and a base length of 663 (66.3%) was actually determined.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A method for gene analysis by hybridization and polymerase extension consisting essentially of:
   a first step of providing a set of degenerate probes that are only single-stranded, each probe having a nucleotide sequence consisting of a combinatorially prescribed, consecutive sequence and the remaining random sequence, wherein the random sequence contains every possible combination of nucleotides given the length of the random sequence;
   a second step of hybridizing a single-stranded nucleic acid analyte derived from the gene to each probe while tolerating some mismatched and multi-sited hybridization;
   a third step of using the hybridized nucleic acid analyte as a template and each probe as a primer to carry out a thermo-cycled polymerase reaction, and extending the primer while tolerating some mismatched and multi-sited polymerase extension;
   a fourth step of separating the extension reaction products obtained from each probe by gel electrophoresis, and determining the base lengths of the extension products to align the probe sequences according to the determined base lengths; and
   a fifth step of graphically realigning the prescribed base sequence of each probe according to an Eulerian path-finding algorithm within the limit of accuracy in determination of the base lengths by gel electrophoresis, and excluding unaligned probe sequences to determine a portion of the base sequence of the nucleic acid analyte.

2. The method for gene analysis according to claim 1, wherein in the fifth step, the full length base sequence of the nucleic acid analyte is determined.

3. The method for gene analysis according to claim 1, wherein each probe is an oligonucleotide represented by $N_1N_2N_3 \ldots N_nX_1X_2 \ldots X_m$ (formula 1), $N_1N_2N_3 \ldots X_1X_2 \ldots X_mN_n$ (formula 2), $N_1N_2N_3 \ldots X_mX_{n-1}N_n \ldots$ (formula 3), $\ldots$ or $X_1X_2 \ldots X_mN_1N_2N_3 \ldots N_{n-1}N_n$ (formula n) wherein $N_1-N_n$ designate any of the four bases A, T, G and C but are random, $X_1-X_m$ designate any of A, T, G and C but are combinatorially predetermined, and m and n are each natural number.

4. The method for gene analysis according to claim 3, wherein the set of degenerate probes is the set of all of the $4^m$ combinations comprising each probe, or a partial subset thereof.

5. The method for gene analysis according to claim 3, wherein m is 3, 4 or 5.

6. The method for gene analysis according to claim 3, wherein n is 5, 6, 7 or 8.

7. The method for gene analysis according to claim 3, wherein m is 4 and n is 6.

8. The method for gene analysis according to claim 1, wherein in the first step there is prepared an array vessel having a number of wells corresponding to the total number of the set of degenerate probes, and each probe is fractionally dispensed into one of the wells.

9. The method for gene analysis according to claim 8, wherein each probe is an oligonucleotide represented by $N_1N_2N_3 \ldots N_nX_1X_2 \ldots X_m$ (formula 1), $N_1N_2N_3 \ldots X_1X_2 \ldots X_mN_n$ (formula 2), $N_1N_2N_3 \ldots X_1X_2 \ldots X_mN_{n-1}N_n$ (formula 3), . . . or $X_1X_2 \ldots X_mN_1N_2N_3 \ldots N_{n-1}N_n$ (formula n) wherein $N_1$–$N_n$ designate any of the four bases A, T, G and C but are random, $X_1$–$X_m$ designate any of A, T, G and C but are combinatorially predetermined, and m and n are each natural number and the total number of the set of single-stranded degenerate probes is $4^m$.

* * * * *

UNITED STATES PATENT AND TRADEMARK OFFICE
CERTIFICATE OF CORRECTION

PATENT NO. : 6,376,184 B1
DATED : April 23, 2002
INVENTOR(S) : Hosoi et al.

Figure 2D:
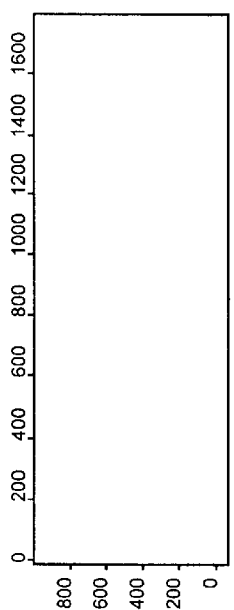
FIG. 2D to $N_1N_2N_3N_4ATGCN_5N_6N_7N$.
Figure 2E:
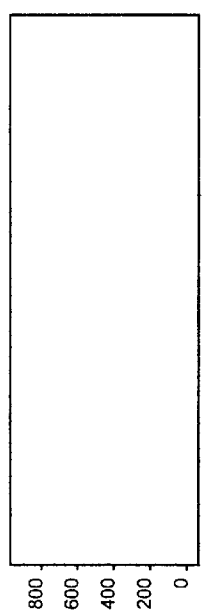
FIG. 2E to $N_1N_2N_3ATGCN_4N_5N_6$. The peaks in each of the charts represent the separated fragments. The horizontal scale in the charts represents fragment base length, and the vertical scale represents fragment intensity (arbitrary units).
Figure 2A:
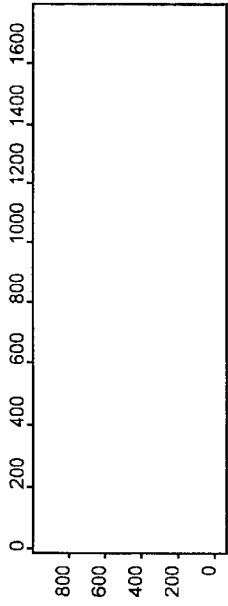
FIG. 2A corresponds to $N_1N_2N_3N_4N_5N_6N_7N_8ATGC$.
Figure 2B:
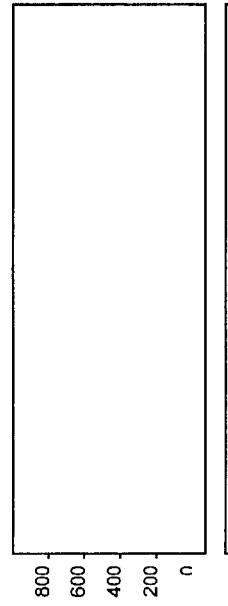
FIG. 2B to $N_1N_2N_3N_4N_5N_6ATGC$.
Figure 2C:
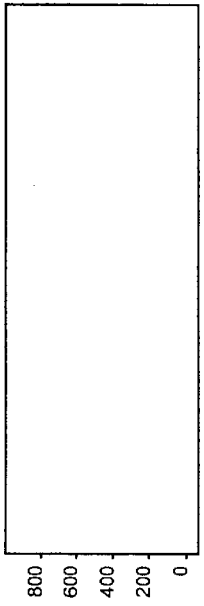
FIG. 2C to $N_1N_2N_3N_4ATGC$.

It is certified that error appears in the above-identified patent and that said Letters Patent is hereby corrected as shown below:

Drawings,
Replace Fig. 2A-2C with:

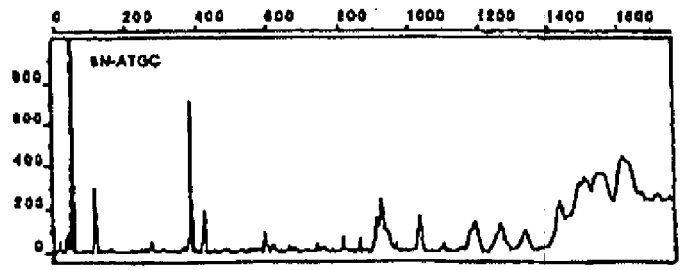

UNITED STATES PATENT AND TRADEMARK OFFICE
CERTIFICATE OF CORRECTION

PATENT NO. : 6,376,184 B1
DATED : April 23, 2002
INVENTOR(S) : Hosoi et al.

It is certified that error appears in the above-identified patent and that said Letters Patent is hereby corrected as shown below:

Drawings (cont.),
Replace Fig. 2D-2E with:

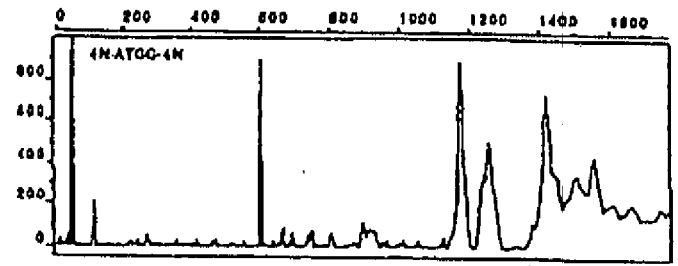

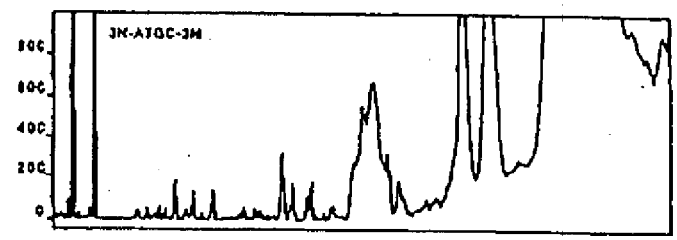

Signed and Sealed this

Twenty-fifth Day of January, 2005

JON W. DUDAS
*Director of the United States Patent and Trademark Office*

SEQUENCE LISTING

<160> NUMBER OF SEQ ID NOS: 16

<210> SEQ ID NO 1
<211> LENGTH: 35
<212> TYPE: DNA
<213> ORGANISM: Artificial Sequence
<220> FEATURE:
<223> OTHER INFORMATION: primer for PCR amplification of bacteriophage
      lambda sequences
<221> NAME/KEY: misc_feature
<223> OTHER INFORMATION: Primer

<400> SEQUENCE: 1
gatgagttcg tgtccgtaca actggcgtaa tcatg                              35

<210> SEQ ID NO 2
<211> LENGTH: 22
<212> TYPE: DNA
<213> ORGANISM: Artificial Sequence
<220> FEATURE:
<223> OTHER INFORMATION: primer for PCR amplification of bacteriophage
      lambda sequences
<221> NAME/KEY: misc_feature
<223> OTHER INFORMATION: Primer

<400> SEQUENCE: 2
gatagctgtc gtcataggac tc                                            22

<210> SEQ ID NO 3
<211> LENGTH: 2000
<212> TYPE: DNA
<213> ORGANISM: Artificial Sequence
<220> FEATURE:
<223> OTHER INFORMATION: DNA amplified by PCR primers of SEQ ID Nos. 1 and 2
<221> NAME/KEY: misc_feature
<223> OTHER INFORMATION: Template

<400> SEQUENCE: 3

```
gatgagttcg tgtccgtaca actggcgtaa tcatggccct tcggggccat ttgtttctct    60
gtggaggagt ccatgacgaa agatgaactg attgcccgtc tccgctcgct gggtgaacaa   120
ctgaaccgtg atgtcagcct gacggggacg aaagaagaac tggcgctccg tgtggcagag   180
ctgaaagagg agcttgatga cacggatgaa actgccggtc aggacacccc tctcagccgg   240
gaaaatgtgc tgaccggaca tgaaaatgag gtgggatcag cgcagccgga taccgtgatt   300
ctggatacgt ctgaactggt cacggtcgtg gcactggtga agctgcatac tgatgcactt   360
cacgccacgc gggatgaacc tgtggcattt gtgctgccgg aacggcgtt tcgtgtctct    420
gccggtgtgg cagccgaaat gacagagcgc ggcctggcca gaatgcaata cgggaggcg    480
ctgtggctga tttcgataac ctgttcgatg ctgccattgc ccgcgccgat gaaacgatac   540
gcgggtacat gggaacgtca gacaccatta atccggtga gcagtcaggt gcggtgatac   600
gtggtgtttt tgatgaccct gaaaatatca gctatgccgg acagggcgtg cgcgttgaag   660
gctccagccc gtccctgttt gtccggactg atgaggtgcg gcagctgcgg cgtggagaca   720
cgctgaccat cggtgaggaa aatttctggg tagatcgggt ttcgccggat gatggcggaa   780
gttgtcatct ctggcttgga cggggcgtac cgcctgccgt taaccgtcgc cgctgaaagg   840
gggatgtatg gccataaaag gtcttgagca ggccgttgaa acctcagcc gtatcagcaa    900
aacggcggtg cctggtgccg ccgcaatggc cattaaccgc gttgcttcat ccgcgatatc   960
gcagtcggcg tcacaggttg cccgtgagac aaaggtacgc cggaaactgg taaggaaag   1020
ggccaggctg aaaagggcca cggtcaaaaa tccgcaggcc agaatcaaag ttaaccgggg   1080
ggatttgccc gtaatcaagc tgggtaatgc gcgggttgtc ctttcgcgcc gcaggcgtcg   1140
taaaaagggg cagcgttcat ccctgaaagg tggcggcagc gtgcttgtgg tgggtaaccg   1200
tcgtattccc ggcgcgttta ttcagcaact gaaaaatggc cggtggcatg tcatgcagcg   1260
tgtggctggg aaaaaccgtt accccattga tgtggtgaaa atcccgatgg cggtgccgct   1320
gaccacggcg ttaaacaaaa tattgagcgg atacggcgtg aacgtcttga aagagctggg   1380
ctatgcgctg cagcatcaac tgaggatggt aataaagcga tgaaacatac tgaactccgt   1440
gcagccgtac tggatgcact ggagaagcat gacaccgggg cgacgttttt tgatggtcgc   1500
cccgctgttt ttgatgaggc ggatttccg gcagttgccg tttatctcac cggcgctgaa    1560
tacacgggcg aagagctgga cagcgatacc tggcaggcgg agctgcatat cgaagttttc   1620
ctgcctgctc aggtgccgga ttcagagctg gatgcgtgga tggagtcccg gatttatccg   1680
gtgatgagcg atatcccggc actgtcagat ttgatcacca gtatggtggc cagcggctat   1740
gactaccggc gcgacgatga tgcgggcttg tggagttcag ccgatctgac ttatgtcatt   1800
acctatgaaa tgtgaggacg ctatgcctgt accaaatcct acaatgccgg tgaaaggtgc   1860
cgggaccacc ctgtgggttt ataaggggag cggtgaccct tacgcgaatc cgctttcaga   1920
cgttgactgg tcgcgtctgg caaaagttaa agacctgacg cccggcgaac tgaccgctga   1980
```

```
gtcctatgac gacagctatc                                                    2000

<210> SEQ ID NO 4
<211> LENGTH: 10
<212> TYPE: DNA
<213> ORGANISM: Artificial Sequence
<220> FEATURE:
<223> OTHER INFORMATION: hypothetical sequence
<221> NAME/KEY: misc_feature
<222> LOCATION: (5)..(10)
<223> OTHER INFORMATION: "n" can be any of a, t, g, or c
<221> NAME/KEY: misc_feature
<222> LOCATION: (1)..(10)
<223> OTHER INFORMATION: Primer

<400> SEQUENCE: 4 aacgnnnnnn                                                                 10

<210> SEQ ID NO 5
<211> LENGTH: 10
<212> TYPE: DNA
<213> ORGANISM: artificial sequence
<220> FEATURE:
<223> OTHER INFORMATION: hypothetical sequence
<221> NAME/KEY: misc_feature
<222> LOCATION: (5)..(10)
<223> OTHER INFORMATION: "n" can be any of a, t, g, or c

<400> SEQUENCE: 5 tacgnnnnnn                                                                 10

<210> SEQ ID NO 6
<211> LENGTH: 10
<212> TYPE: DNA
<213> ORGANISM: Artificial Sequence
<220> FEATURE:
<223> OTHER INFORMATION: hypothetical sequence
<221> NAME/KEY: misc_feature
<222> LOCATION: (5)..(10)
<223> OTHER INFORMATION: "n" can be any of a, t, g, or c

<400> SEQUENCE: 6 gacgnnnnnn                                                                 10

<210> SEQ ID NO 7
<211> LENGTH: 10
<212> TYPE: DNA
<213> ORGANISM: Artificial Sequence
<220> FEATURE:
<223> OTHER INFORMATION: hypothetical sequence
<221> NAME/KEY: misc_feature
<222> LOCATION: (5)..(10)
<223> OTHER INFORMATION: "n" can be any of a, t, g, or c

<400> SEQUENCE: 7 cacgnnnnnn                                                                 10

<210> SEQ ID NO 8
<211> LENGTH: 12
<212> TYPE: DNA
<213> ORGANISM: Artificial Sequence
<220> FEATURE:
<223> OTHER INFORMATION: hypothetical sequence
<221> NAME/KEY: misc_feature
<222> LOCATION: (5)..(12)
<223> OTHER INFORMATION: "n" can be any of a, t, g, or c
```

```
<400> SEQUENCE: 8
cgtannnnnn nn                                                              12

<210> SEQ ID NO 9
<211> LENGTH: 10
<212> TYPE: DNA
<213> ORGANISM: Artificial Sequence
<220> FEATURE:
<223> OTHER INFORMATION: hypothetical sequence
<221> NAME/KEY: misc_feature
<222> LOCATION: (5)..(10)
<223> OTHER INFORMATION: "n" can be any of a, t, g, or c

<400> SEQUENCE: 9 cgtannnnnn                                                                 10

<210> SEQ ID NO 10
<211> LENGTH: 8
<212> TYPE: DNA
<213> ORGANISM: Artificial Sequence
<220> FEATURE:
<223> OTHER INFORMATION: hypothetical sequence
<221> NAME/KEY: misc_feature
<222> LOCATION: (5)..(8)
<223> OTHER INFORMATION: "n" can be any of a, t, g, or c

<400> SEQUENCE: 10 cgtannnn                                                                    8

<210> SEQ ID NO 11
<211> LENGTH: 12
<212> TYPE: DNA
<213> ORGANISM: Artificial Sequence
<220> FEATURE:
<223> OTHER INFORMATION: hypothetical sequence
<221> NAME/KEY: misc_feature
<222> LOCATION: (1)..(4)
<223> OTHER INFORMATION: "n" can be any of a, t, g, or c
<221> NAME/KEY: misc_feature
<222> LOCATION: (9)..(12)
<223> OTHER INFORMATION: "n" can be any of a, t, g, or c

<400> SEQUENCE: 11
nnnncgtann nn                                                              12

<210> SEQ ID NO 12
<211> LENGTH: 10
<212> TYPE: DNA
<213> ORGANISM: Artificial Sequence
<220> FEATURE:
<223> OTHER INFORMATION: hypothetical sequence
<221> NAME/KEY: misc_feature
<222> LOCATION: (1)..(3)
<223> OTHER INFORMATION: "n" can be any of a, t, g, or c
<221> NAME/KEY: misc_feature
<222> LOCATION: (8)..(10)
<223> OTHER INFORMATION: "n" can be any of a, t, g, or c

<400> SEQUENCE: 12 nnncgtannn                                                                 10

<210> SEQ ID NO 13
<211> LENGTH: 25
<212> TYPE: DNA
<213> ORGANISM: Artificial Sequence
<220> FEATURE:
<223> OTHER INFORMATION: predicted sequence
<221> NAME/KEY: misc_feature
<223> OTHER INFORMATION: Part of the template
```

```
<400> SEQUENCE: 13
agctatgccg gacagggcgt gcgcg                                              25

<210> SEQ ID NO 14
<211> LENGTH: 17
<212> TYPE: DNA
<213> ORGANISM: Artificial Sequence
<220> FEATURE:
<223> OTHER INFORMATION: predicted sequence
<221> NAME/KEY: misc_feature
<223> OTHER INFORMATION: Part of the template

<400> SEQUENCE: 14
cgttgaaggc tccagcc                                                       17

<210> SEQ ID NO 15
<211> LENGTH: 17
<212> TYPE: DNA
<213> ORGANISM: Artificial Sequence
<220> FEATURE:
<223> OTHER INFORMATION: Predicted Sequence
<221> NAME/KEY: misc_feature
<223> OTHER INFORMATION: Part of the template

<400> SEQUENCE: 15
aagggccagg ctgaaaa                                                       17

<210> SEQ ID NO 16
<211> LENGTH: 10
<212> TYPE: DNA
<213> ORGANISM: Artificial Sequence
<220> FEATURE:
<223> OTHER INFORMATION: Predicted Sequence
<221> NAME/KEY: misc_feature
<223> OTHER INFORMATION: Part of the template

<400> SEQUENCE: 16
aagggccacg                                                               10
```